United States Patent [19]

Suzuki et al.

[11] 4,330,558

[45] May 18, 1982

[54] PHARMACEUTICAL COMPOSITION AND METHOD FOR TREATING PERIPHERAL ORTHOSTATIC HYPOTENSION

[75] Inventors: Tomokazu Suzuki, No. 9-30-307, Okamoto 4-chome, Higashinada-ku, Kobe-shi, Hyogo-ken; Akira Hayashi, No. 290-1-210, Yamadaue, Suita-shi, Osaka-fu; Yuichi Yamamura, No. 1-9-22, Nigawatakadai, Takarazuka-shi, Hyogo-ken, all of Japan

[73] Assignees: Sumitomo Chemical Company, Limited, Osaka; Tomokazu Suzuki, Kobe; Akira Hayashi, Suita; Yuichi Yamamura, Takarazuka, all of Japan

[21] Appl. No.: 173,620

[22] Filed: Jul. 30, 1980

[30] Foreign Application Priority Data

Jan. 23, 1980 [JP] Japan ................................. 55-7234

[51] Int. Cl.$^3$ ............................................. A61K 31/195
[52] U.S. Cl. ................................................... 424/319
[58] Field of Search ........................................ 424/319

[56] References Cited

U.S. PATENT DOCUMENTS 3,920,728  11/1975  Hegedus et al. .................. 420/300 X

FOREIGN PATENT DOCUMENTS 50-49252   4/1975  Japan .
54-19931   2/1979  Japan .
54-106483  9/1979  Japan .

OTHER PUBLICATIONS

C.A. 68, Entry 58294u (1968).
C.A. 68, Entry 76839e (1968).
C.A. 74, Entry 97645c (1971).
C.A. 75, Entry 72244d (1971) & 8th Coll. Formula Index, p. 2470f.
Goodman & Gilman, "Pharm. Basis of Therap.," 3rd ed. (1965), p. 512.

*Primary Examiner*—Frank Cacciapaglia, Jr.
*Attorney, Agent, or Firm*—Birch, Stewart, Kolasch & Birch

[57] ABSTRACT

A method for treating peripheral orthostatic hypotension which comprises administering DL- or L-threo-3,4-dihydroxyphenylserine or a pharmaceutically acceptable acid addition salt thereof to a subject suffering from the disease. The composition may be administered either orally or parenterally.

3 Claims, 8 Drawing Figures

PHARMACEUTICAL COMPOSITION AND METHOD FOR TREATING PERIPHERAL ORTHOSTATIC HYPOTENSION

The present invention relates to a pharmaceutical composition for treating peripheral orthostatic hypotension, which comprises as an active ingredient DL- or L-threo-3,4-dihydroxyphenylserine or a pharmaceutically acceptable acid addition salt thereof and a method for treating peripheral orthostatic hypotension with the active compound.

Orthostatic hypotension is caused by various diseases and is classified as follows:

"Central" type
Shy-Drager syndrome
intracranial tumor
Parkinsonism
"Peripheral" type
diabetes mellitus
angitis
alcoholism
amyloidosis
acute pan-dysautonomia
familial dysautonomia (Riely-Day syndrome)
syphilis
drug-induced orthostatic hypotension
idiopathic orthostatic hypotension There is so far no single drug that has proved effective in the treatment of orthostatic hypotension. Recently, it was reported that tyramine combined with a monoamine oxidase inhibitor is effective in the treatment of the "central" type of orthostatic hypotension. However, no reliable and effective drug for the treatment of the "peripheral" type of orthostatic hypotension in which the deficit appears to be at the sympathetic nerves has yet been found.

While studying the pathophysiology of familial amyloid poly-neuropathy (FAP) as a model of "dysautonomia syndrome", the present inventors have found that DL- or L-threo-3,4-dihydroxyphenylserine (threo-DOPS) is effective on orthostatic hypotension, inducing substantial and sustained elevation of blood pressure. Application of DL-threo-DOPS to various kinds of orthostatic hypotension proved that threo-DOPS is a novel drug for treating "peripheral" type of orthostatic hypotension.

It has already been known that L-threo-DOPS is converted to (−) norepinephrine by aromatic L-amino acid decarboxylase in the living body. On the other hand, it is also known that norepinephrine is one of the catecholamines and is useful as a hypertensor. Therefore, it may generally be expected that DOPS has properties suitable as a hypertensor. However, the effect of DOPS in the human body can not necessarily be estimated since, contrary to the above, DOPS is reported as a compound having anti-hypertensive action in a certain case as in Japanese Patent Publication (unexamined) No. 49252/1975.

The pharmacological tests described hereinafter, revealed that threo-DOPS has a selective effect on "peripheral" orthostatic hypotension, while it does not have a significant effect on blood pressure of normal subjects and of patients suffering from "central" orthostatic hypotension.

One object of the present invention is to provide a novel pharmaceutical composition for treating "peripheral" orthostatic hypotension. Another object of the present invention is to provide a method for preparation of a pharmaceutical composition for treating "peripheral" orthostatic hypotension. Still another object of the present invention is to provide a method for treating orthostatic hypotension.

These objects as well as other objects and advantages of the present invention will become apparent to those skilled in the art from the following description by reference to the accompanying drawings in which.

The present invention provides a pharmaceutical composition for treating peripheral orthostatic hypotension which comprises as an active ingredient threo-DOPS or a pharmaceutically acceptable acid addition salt thereof and a pharmaceutically acceptable carrier or diluent. The present invention also includes a method of preparation of such a pharmaceutical composition which comprises admixing the active ingredient with a pharmaceutically acceptable carrier or diluent and a method for treating "peripheral" orthostatic hypotension which comprises administering the active compound or a pharmaceutical composition containing it to a subject suffering from the disease.

In general, threo-DOPS exists as optical isomers and there are the L- and D-isomers as well as the racemic DL-isomer. The term "threo-DOPS" used herein means DL-threo-DOPS and L-threo-DOPS. According to the pharmacological tests of the present invention, the L-isomer is about twice as effective as the DL-isomer and it shows the same effect as the DL-isomer in one half the amount thereof.

The pharmacological tests of threo-DOPS are illustrated hereinafter by reference to the accompanying figures.

1. Effect of DL-threo-DOPS on adrenergic activity in patients with FAP (1) Intravenous drip infusion test of DL-threo-DOPS The test was carried out by administering 200 mg of DL-threo-DOPS in 400 ml of isotonic sodium chloride solution over 2 hours to four persons (2 normal persons and 2 FAP patients) by intravenous drip infusion (1.7 mg/min.). Changes in pulse rate and blood pressure were determined. The results are shown in FIG. 1.

Figure 1:
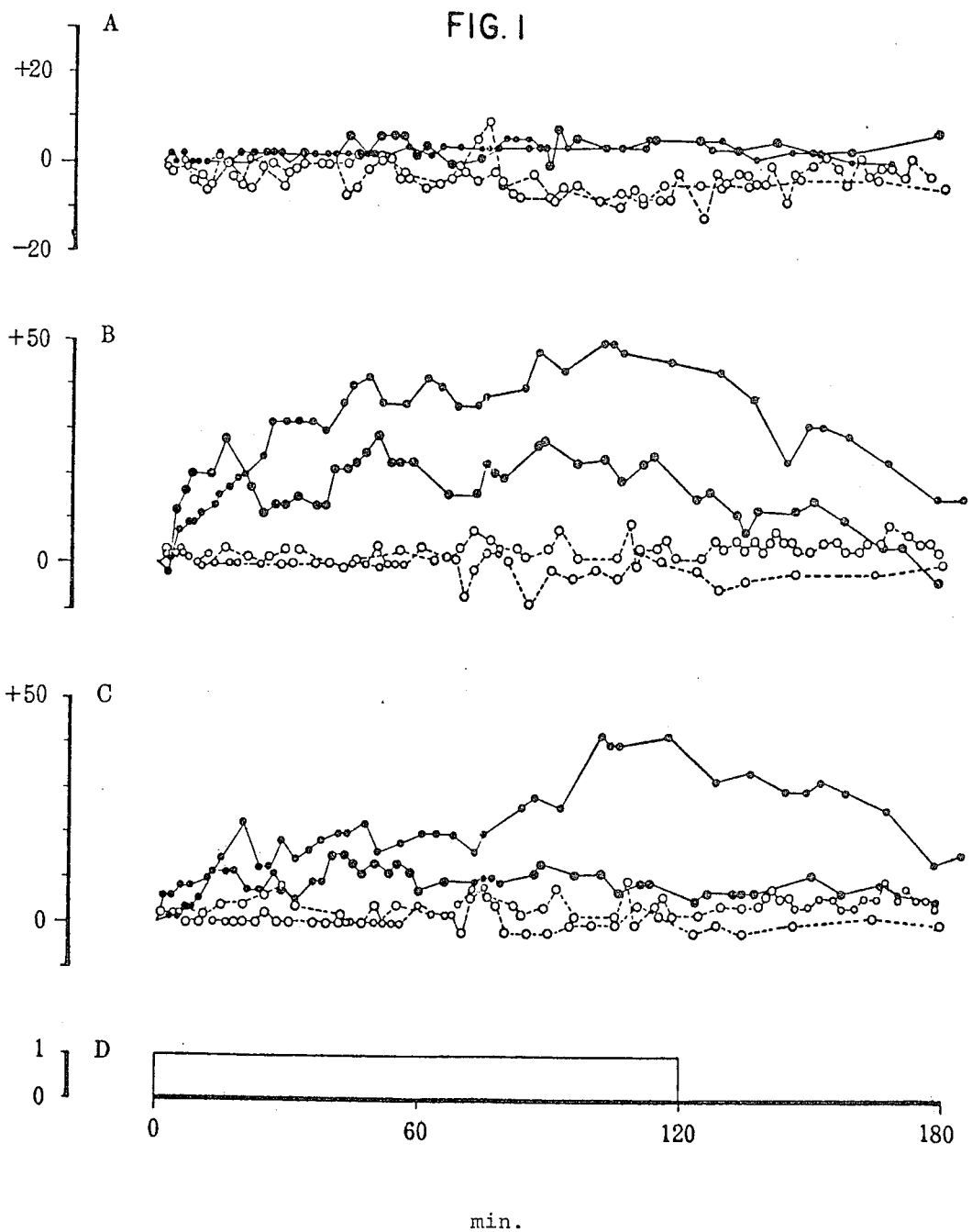
FIG. 1 shows the results obtained by intravenous drip infusion of DL-threo-DOPS as is explained hereinafter.

In the graphs A to D of FIG. 1, the abscissa axes indicate time (min.) and the ordinate axes indicate changes in pulse rate, maximum blood pressure (mmHg) and minimum blood pressure (mmHg), and drip infusion rate of DL-threo-DOPS (mg/min.), respectively. In the graphs A to C, the symbol o indicates normal subjects (2 persons) and ●, FAP patients (2 persons).

As shown in FIG. 1, the administration of DL-threo-DOPS did not change either pulse rate or blood pressure in the two normal persons, whereas a sensitive hypertensive response was observed in the two FAP patients. Further, the time course of the response was gradual and sustained. These properties are hardly observed in conventional hypertensors and are characteristic of threo-DOPS.

(2) Oral administration test of DL-threo-DOPS

The test was carried out by administering orally 600 mg of DL-threo-DOPS to nine persons (4-normal persons and 5 FAP patients). Plasma norepinephrine levels and blood pressure were determined. The results obtained from the FAP patients are shown in FIG. 2.

Figure 2:
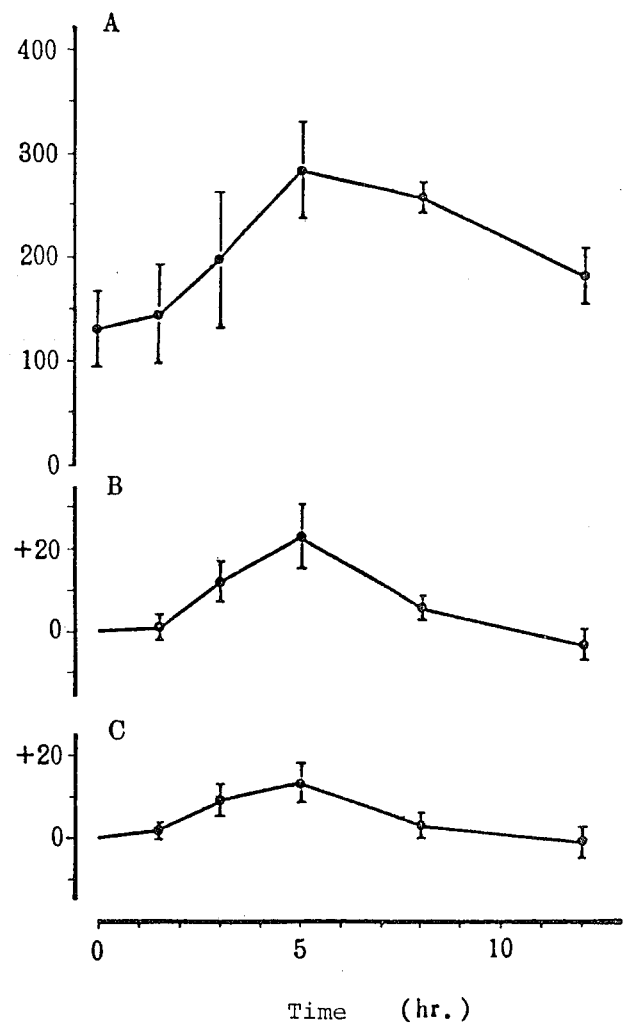
FIG. 2 shows the results obtained by oral administration of DL-threo-DOPS to FAP patients.

In the graphs A to C of FIG. 2, the abscissa axes indicate time (hrs.) and the ordinate axes indicate plasma norepinephrine level (pg/ml), change in maximum blood pressure (mmHg) and minimum blood pressure (mmHg), respectively. The results are expressed as mean±S.E.

As shown in FIG. 2, gradual and sustained hypertensive action which reaches the peak 5 hours after oral administration of DL-threo-DOPS was observed in patients with FAP, whereas no significant change in blood pressure was observed in normal subjects. Change in plasma norepinephrine level was almost parallel with that of blood pressure and was restored to the normal level 5 hours after oral administration of DL-threo-DOPS.

The results mean that DL-threo-DOPS administered orally is absorbed in the intestine and is converted to (−) norepinephrine by aromatic L-amino acid decarboxylase which is distributed in various organs as well as nerves and then, the norepinephrine formed elicits a hypertensive action.

(3) Long term oral administration of DL-threo-DOPS

The clinical trial was carried out according to a simple blind test procedure. DL-threo-DOPS was orally administered to six FAP patients for 4 weeks (1.2 g of daily dosage, twice per day at 8 a.m. and 8 p.m.). The patients refrained from taking any drug for one week before administration of DL-threo-DOPS. After 4 weeks of administration period of DL-threo-DOPS, the patients were given placebos containing lactose. In order to estimate the clinical effect of DL-threo-DOPS, a change in symptom was recorded on a chart by the patients themselves, and blood pressure in the supine position was measured at 7 a.m., 11 a.m., 1 p.m., 4 p.m. and 8 p.m. during the test period. The results for one FAP patient are shown in FIG. 3.

Figure 3:
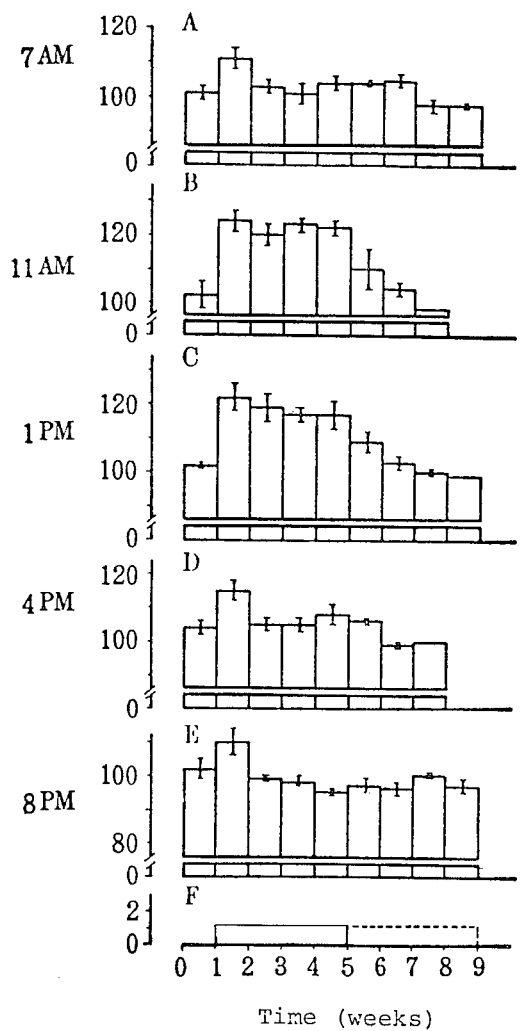
FIG. 3 shows the results obtained by orally administering DL-threo-DOPS to a FAP patient for 4 weeks.

In the graphs A to F of FIG. 3, the abscissa axes indicate time (weeks) and the ordinate axes indicate maximum blood pressure (mmHg) measured at 7 a.m., 11 a.m., 1 p.m., 4 p.m. and 8 p.m. and dosage of DL-threo-DOPS (g/day), respectively. The results are expressed as mean±S.E.

During the administration period of DL-threo-DOPS, a significant rise of blood pressure was observed at 11 a.m. and 1 p.m. (corresponding to 3 and 5 hours after administration of DL-threo-DOPS, respectively) in the three patients suffering from orthostatic hypotension. Dizziness and giddiness caused by orthostatic hypotension were mitigated and activity of daily living was restored. No side effect was observed.

2. Effect on DL-threo-DOPS on blood pressure in patients suffering from various kinds of orthostatic hypotension Under the same condition as in FAP, DL-threo-DOPS was administered intravenously to patients suffering from familial diabetes mellitus, aortitis syndrome, idiopathic orthostatic hypotension, acute pan-dysautonomia and ectopic pineal tumor, respectively. Changes in pulse rate and blood pressure were determined. The results are shown in FIGS. 4 to 8.

In the graphs A to D of FIGS. 4, 5, 6, 7 and 8, the abscissa axes indicate time (min.) and the ordinate axes indicate change in pulse rate, maximum blood pressure (mmHg) and minimum blood pressure (mmHg), and drip infusion rate of DL-threo-DOPS (mg/min.), respectively.

The results are explained in detail below.

Figure 4:
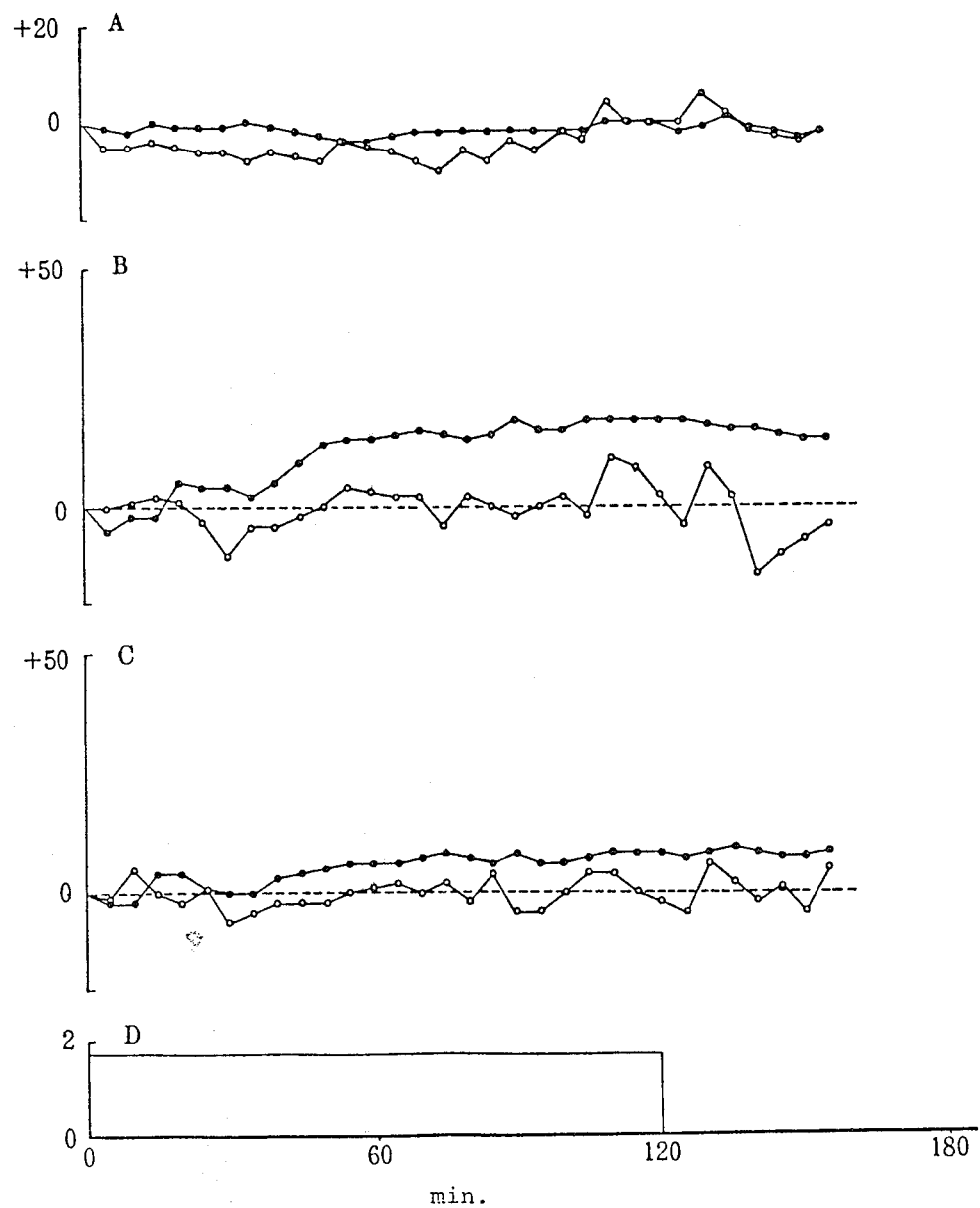
FIGS. 4 to 8 illustrate the results obtained by intravenous drip infusion of DL-threo-DOPS into patients suffering from familial diabetes mellitus, aortitis syndrome, idiopathic orthostatic hypotension, acute pan-dysautonomia, and ectopic pineal tumor, respectively.

(1) Diabetes mellitus observed in siblings (FIG. 4)

Patient A: woman, 50 years old (asymptomatic orthostatic hypotension was observed). Patient B: man, 46 years old (no orthostatic hypotension was observed). Of patients A and B, patient A showed pressor response. In the graphs A to C of FIG. 4, the symbol ● indicates the patient A and o, the patient B.

Figure 5:
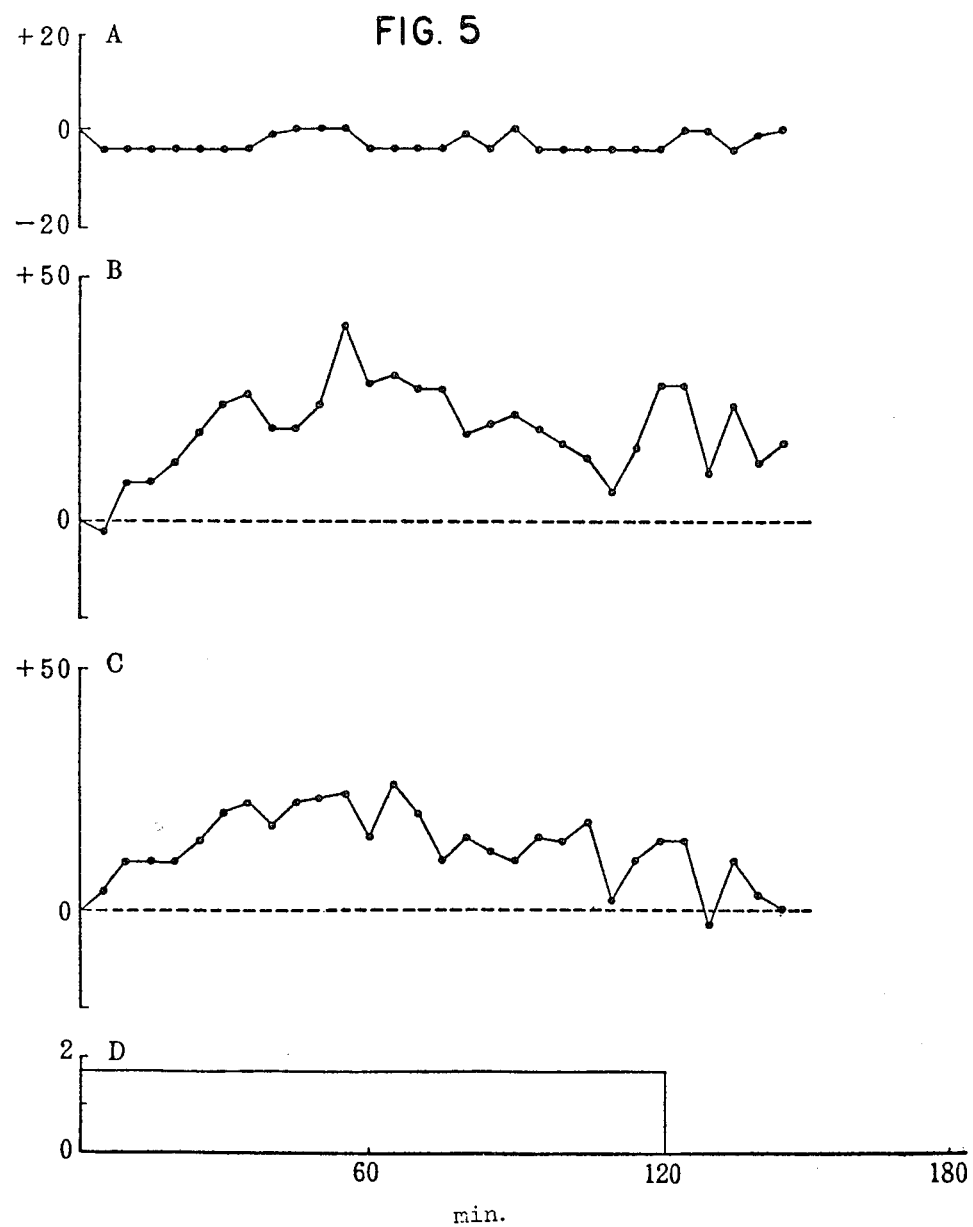

(2) Aortitis syndrome (FIG. 5)

Patient: woman, 65 years old. Pressor response was observed.

Figure 6:
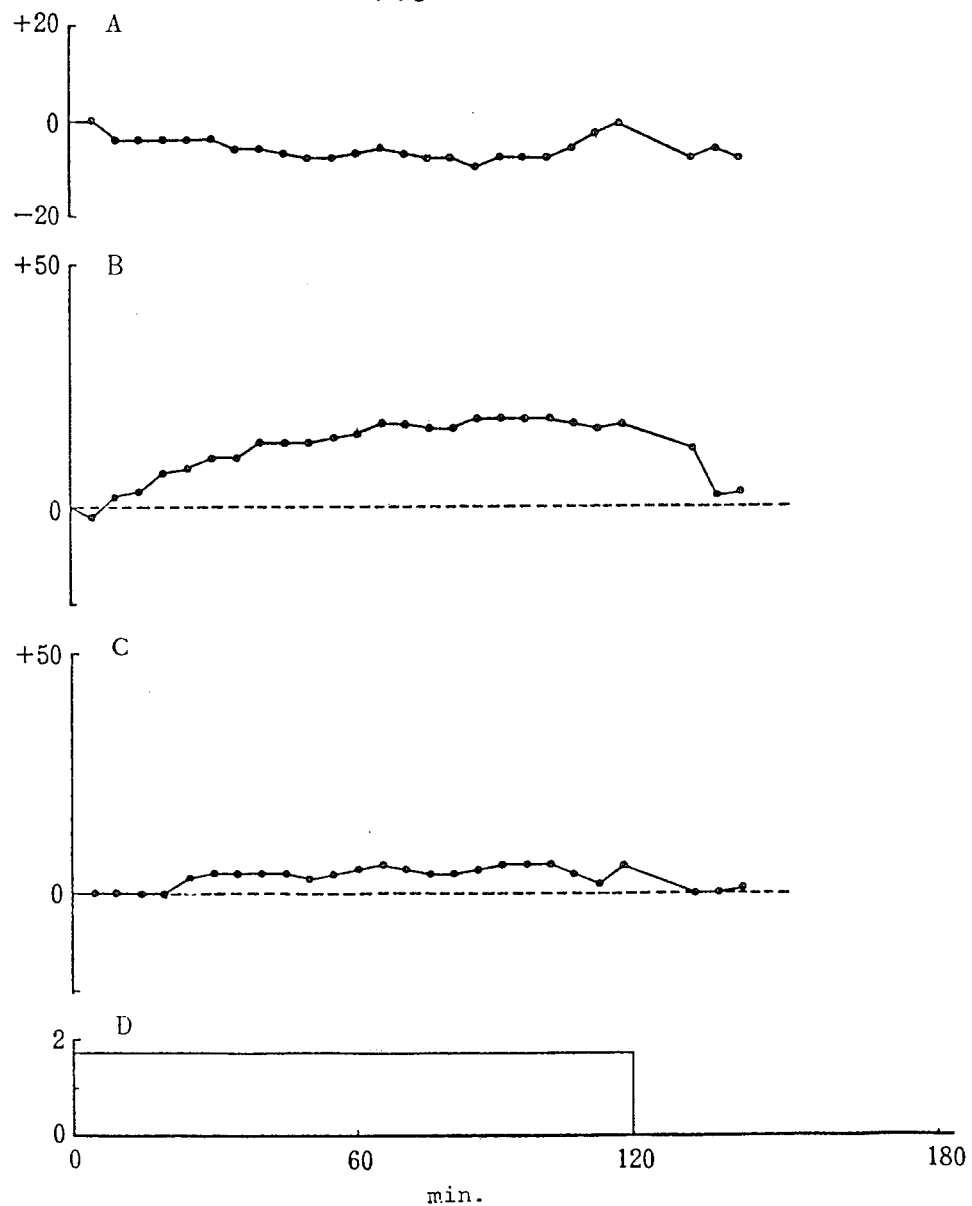

(3) Idiopathic orthostatic hypotension (FIG. 6)

Patient: man, 68 years old. Pressor response was observed.

Figure 7:
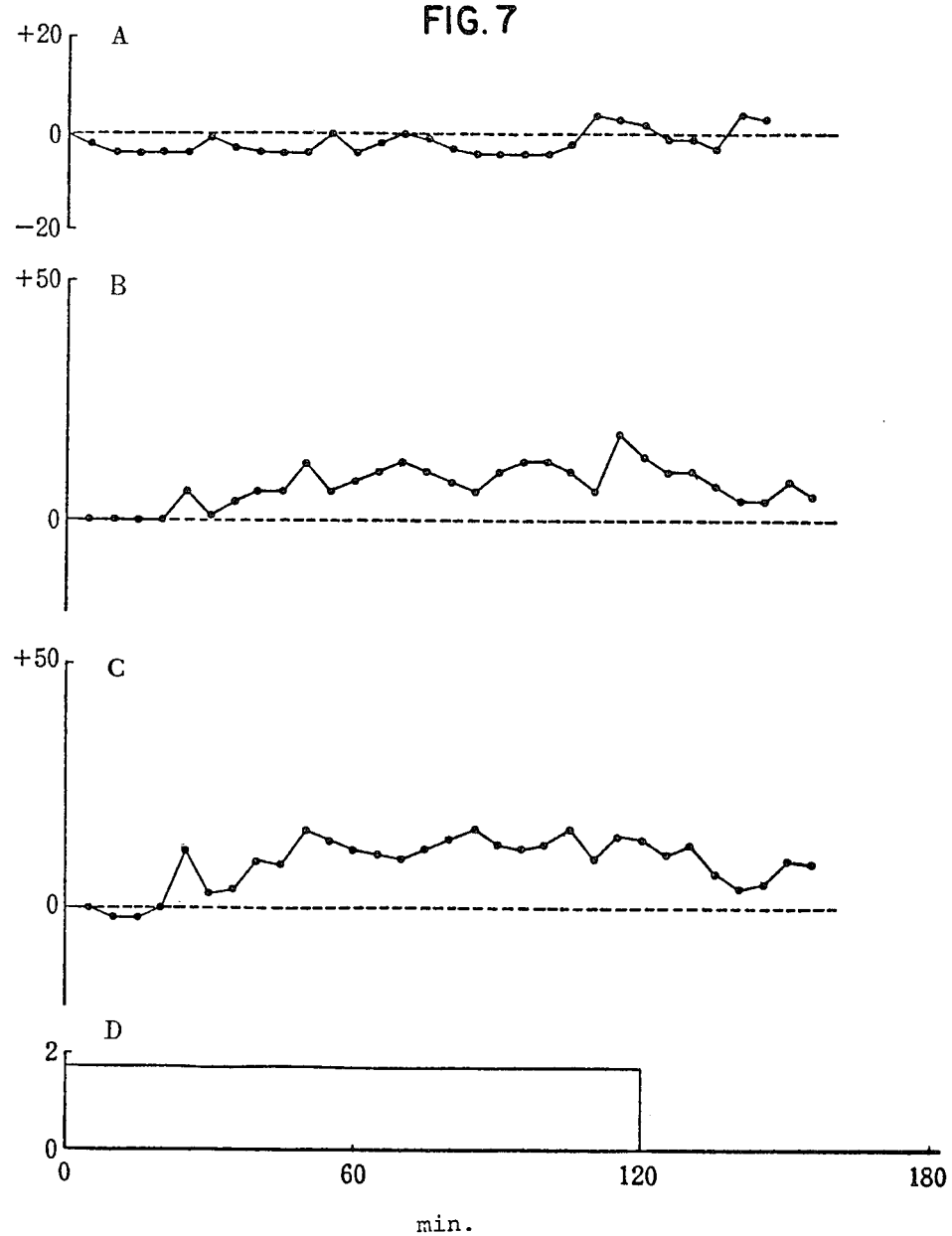

(4) Acute pan-dysautonomia (FIG. 7)

Patient: man, 25 years old. Pressor response was observed.

Figure 8:
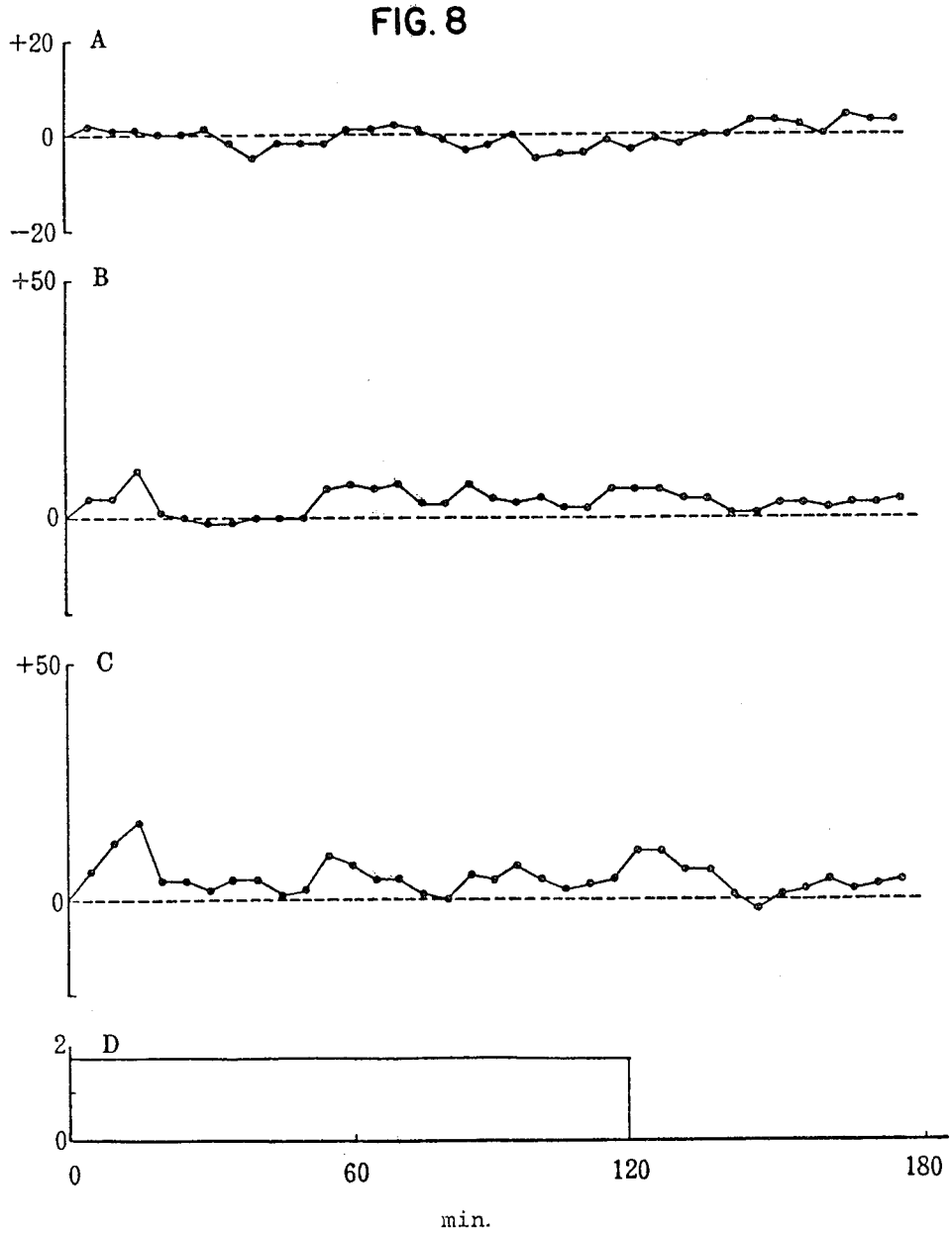

(5) Ectopic pineal tumor (FIG. 8)

Patient: man, 24 years old. Pressor response was not observed.

As is shown in the above results of (1) to (5), DL-threo-DOPS induced pressor response in case of (1) to (4), but not in case of (5). This means that DL-threo-DOPS has a selective effect on the "peripheral" type of orthostatic hypotension. It is supposed that this phenomenon is due to denervation supersensitivity of adrenergic receptors in the sympathetic nervous system.

Threo-DOPS used in the present invention is already known and can be prepared according to a known method such as, for example, that described in Japanese Patent Publication (unexamined) No. 19931/1979 or Japanese Patent Application No. 106483/1979.

A pharmaceutically acceptable acid addition salt of threo-DOPS can be also used in the present invention. Examples of the acid addition salts are those formed with an inorganic acid such as, hydrochloric acid, hydrobromic acid, sulfuric acid or the like, or an organic acid such as, fumaric acid, citric acid, tartaric acid, succinic acid or the like.

The pharmaceutical composition of the present invention contains as an active ingredient threo-DOPS or a pharmaceutically acceptable acid addition salt thereof in an amount effective for treating peripheral orthostatic hypotension, and a pharmaceutically acceptable carrier or diluent such as, starch, lactose, dextrin, talc, magnesium stearate, calcium carboxymethyl cellulose, finely crystalline cellulose or the like.

The pharmaceutical composition of the present invention can be prepared in a conventional dosage from for oral administration such as, a tablet, capsule, syrup, liquid suspension or the like. The composition can be also prepared in an injectable liquid dosage form such as, a solution, emulsion, liquid suspension or the like. The composition can further contain other additives such as an excipient (e.g. glucose, gelatin, etc.), binder (e.g. hydroxypropyl cellulose, polyvinyl alcohol, etc.), stabilizer (e.g. ascorbic acid, sodium bisulfite, etc.) and the like. Further, in case of an injectable dosage form, it can contain a buffering agent (e.g. citric acid, sodium citrate, glycine, etc.), solubilizer (e.g. propylene glycol, polysorbate 80, lecithin, etc.), agent to make the solution isotonic (e.g. sodium chloride, boric acid, etc.) and the like.

The pharmaceutical composition of the present invention can be prepared, for example, by mixing, granulating and compressing or dissolving the active ingredient together with other ingredients as suitable for the desired form of composition. The composition is preferably in dosage unit form and each dosage unit preferably contains the active ingredient in an amount of from about 50 mg to about 500 mg.

In accordance with the method for treating peripheral orthostatic hypotension of the present invention, the active compound, threo-DOPS or a pharmaceutically acceptable acid addition salt thereof, can be administered to the subject being treated orally or parenterally in an effective amount for the particular treatment. The required dosage will vary with the dosage form, the particular condition being treated and the serverity of the condition. For example, in case of oral administration, the active compound will be administered to an adult in the daily dosage of from about 0.1 g to about 6 g. In case of intravenous injection, the compound will be administered to an adult in the daily dosage of from about 0.1 g to about 5 g. The compound will be administered one to several times per day.

Toxicity of threo-DOPS is extremely low. $LD_{50}$ value in mice is more than 10 g/kg (p.o.) and about 10 g/kg (i.p.). Therefore, it is believed that any harmful effect would not be produced in so far as the compound is administered in the above described effective amount and, in fact, no side effect is observed clinically.

The following example illustrate a process for preparing a pharmaceutical composition of the present invention but is not to be construed to limit the scope thereof.

EXAMPLE 2000 g of threo-DOPS, 830 g of lactose, 150 g of calcium carboxymethyl cellulose and 20 g of magnesium stearate were weighed and mixed together in a V-shaped blender for about 30 minutes and then pulverized in a hammer mill.

The powder thus obtained was filled in hard capsules to obtain a hard capsule containing about 300 mg of threo-DOPS per capsule.

What is claimed is:

1. A method for treating peripheral orthostatic hypotension which comprises orally or parenterally administering DL- or L-threo-3,4-dihydroxyphenylserine or a pharmaceutically acceptable acid addition salt thereof in an amount of from about 0.1 g to about 6 g per day to a human patient suffering from the disease until an intended result is obtained.

2. A method for treating peripheral orthostatic hypotension according to claim 1, wherein DL-threo-3,4-dihydroxyphenylserine or a pharmaceutically acceptable acid addition salt thereof is administered.

3. A method for treating peripheral orthostatic hypotension according to claim 1, wherein L-threo-3,4-dihydroxyphenylserine or a pharmaceutically acceptable acid addition salt thereof is administered.

* * * * *